United States Patent [19]

Lee, Jr.

[11] Patent Number: 4,943,293
[45] Date of Patent: Jul. 24, 1990

[54] SURGICAL PIN SITE SHIELD

[75] Inventor: Harry E. Lee, Jr., Southaven, Miss.

[73] Assignee: Engineering & Precision Machining, Inc., Memphis, Tenn.

[21] Appl. No.: 410,277

[22] Filed: Sep. 21, 1989

[51] Int. Cl.$^5$ .................................................. A61F 5/04
[52] U.S. Cl. ........................................ 606/96; 128/888
[58] Field of Search ................... 128/888, 889; 606/96, 606/87, 104, 97, 98, 59

[56] References Cited

U.S. PATENT DOCUMENTS

| | | | |
|---|---|---|---|
| 679,918 | 8/1901 | Shears | 128/888 |
| 3,782,377 | 1/1974 | Rychlick | 128/888 |
| 4,399,816 | 8/1983 | Spangler | 128/888 |
| 4,641,641 | 2/1987 | Strock | 128/888 |

FOREIGN PATENT DOCUMENTS 0003090 of 1902 United Kingdom ................ 128/888

*Primary Examiner*—Robert A. Hafer
*Assistant Examiner*—Michael A. Brown
*Attorney, Agent, or Firm*—Walker & McKenzie

[57] ABSTRACT

A pin site shield is described for covering the entry or exit site of a surgical pin such as a halo pin, external fixation pin, traction pin, or surgical wire. The pin site shield comprises a collar having a slot for receipt of the surgical pin, a surgical sponge attached to the collar, and means for securing the pin in the slot. The surgical sponge includes a foam pad and a tricot material attached to the foam pad on the side remote from the collar. The surgical sponge has a slit in substantial registration with the slot in the collar, allowing the surgical pin to pass inwardly and outwardly within the slot. Preferably, the collar includes a tapped hole passing through a top side of the slot, and a screw inserted into the tapped hole secures the pin in the slot. The collar also preferably includes a nib on the bottom side of the slot for further assistance in securing the pin in the slot. Typically the tapped hole will form an acute angle with the slot for entrapment of a range of sizes of surgical pins, from traction pins to surgical wires, in the corner of the slot.

9 Claims, 2 Drawing Sheets

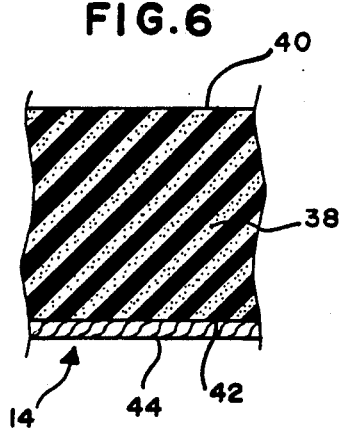
FIG. 6
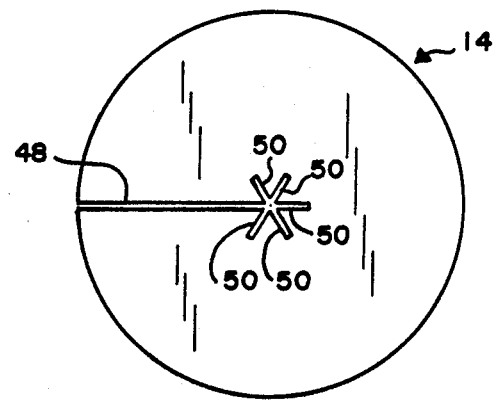
FIG. 7
FIG. 8
FIG. 9
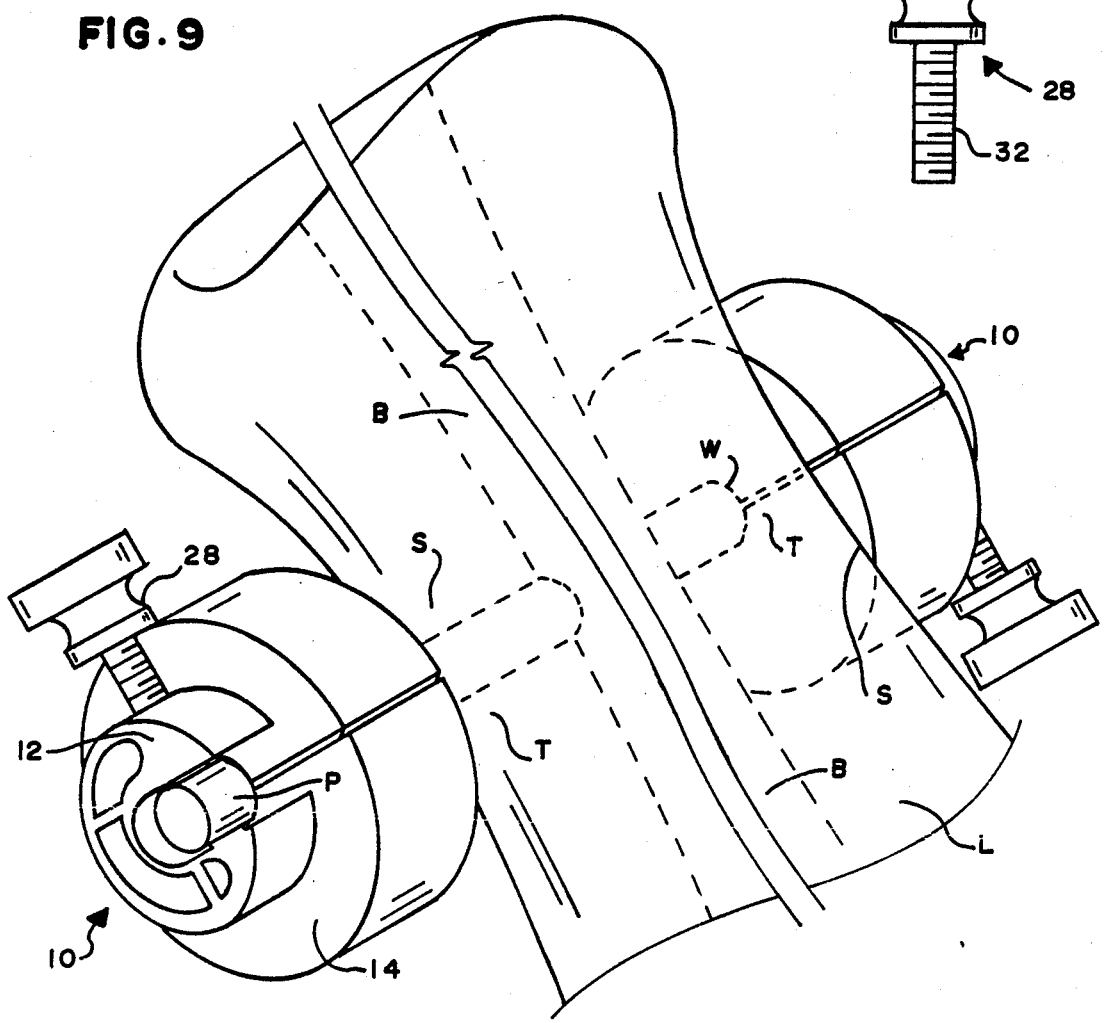

SURGICAL PIN SITE SHIELD

BACKGROUND OF THE INVENTION

1. Field of the Invention:

The present invention relates, in general, to medical devices, and particularly to a surgical dressing for covering the entry or exit site of a surgical pin such as a halo pin, external fixation pin, traction pin, or surgical wire. These entry or exit sites are wounds subject to microbial contamination, and as such, require a dressing saturated with an appropriate antiseptic to prevent infection.

2. Information Disclosure Statement:

Prior to the present invention, patients requiring one or more surgical pins would have the entry or exit sites of the surgical pins wrapped in gauze soaked in antiseptic, such as betadine or a saline solution, to prevent infection. The gauze frequently tends to slide away from the wound, exposing the site to infection. The rate of infection is also increased because there is nothing to prevent the movement of soft tissue around the pin site as the patient changes position. The appearance of the wound where the surgical pin enters or exits the skin is unsightly, causing psychological trauma in some patients, especially children. The substantial time required to change such a dressing, together with the unappealing appearance, tends to reduce the patient compliance with a required daily changing of the dressing. Also, clips have been utilized to hold sponges onto Ilizarov wires. These clips are disadvantageous in that they slide on the wires and can easily pop off of the wires. Thus, the clips slide away from the wound with no soft tissue stability being maintained, and with the exposure to some extent of the unsightly wound area. The present invention overcomes these deficiencies.

SUMMARY OF THE INVENTION

The present invention is directed toward providing an improved device for covering the entry or exit site of a surgical pin such as a halo pin, external fixation pin, traction pin, or surgical wire.

The present invention further provides an improved means for applying an antiseptic to the wound at a surgical pin site.

It is an object of the present invention to prevent or reduce the incidence of pin site infections in patients with surgical pins or an external fixation device.

The present invention is further directed toward reducing the time required to change the dressing at a pin site wound.

It is an object of the present invention to reduce or conceal the unsightly appearance of a surgical pin site.

It is a further object of the present invention to provide means for stabilizing the soft tissue around the entry or exit site of a surgical pin or external fixation device.

BRIEF DESCRIPTION OF THE DRAWINGS

FIG. 6 is an enlarged cross section of a portion of the surgical sponge, showing the construction of tricot material attached to a foam pad.

FIG. 7 is a rear view of the preferred embodiment of the surgical sponge.

FIG. 8 is a view of the screw, which is one possible embodiment of the means for securing the surgical pin to the pin site shield.

FIG. 9 is a perspective view showing the assembled pin site shield attached to a surgical pin at a pin site wound.

DESCRIPTION OF THE PREFERRED EMBODIMENT

Figure 1:
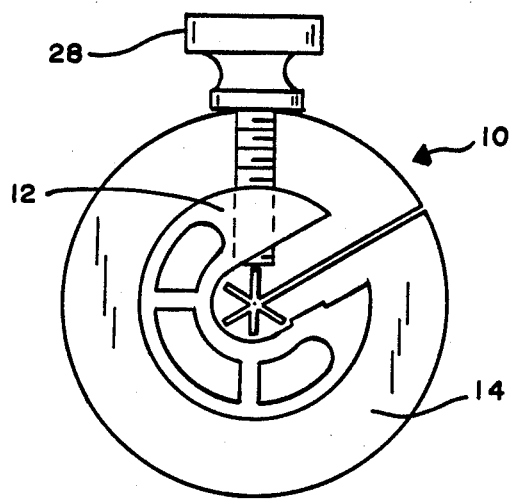
FIG. 1 is a perspective view of the assembled pin site shield.
Figure 2:
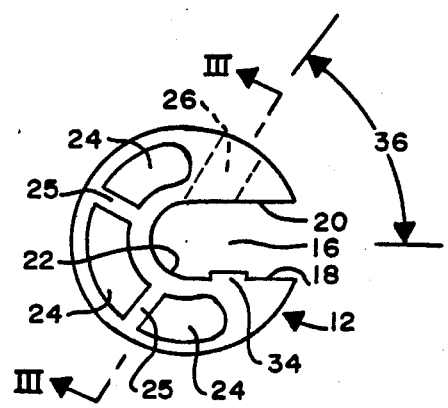
FIG. 2 is a front view of the collar.
Figure 4:
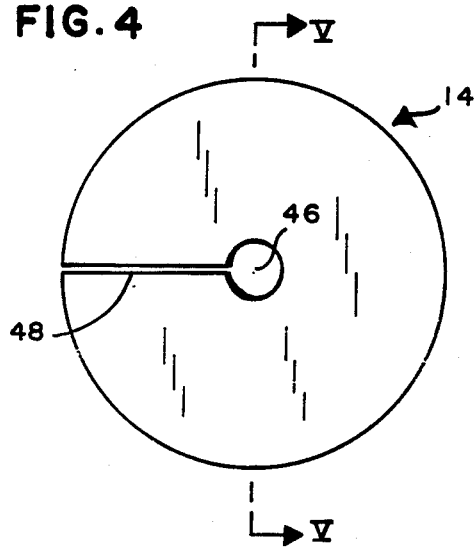
FIG. 4 is a rear view of one embodiment of the surgical sponge.

As seen in FIGS. 1, 2, and 4, the pin site shield 10 of the present invention comprises a collar 12 and a surgical sponge 14 attached to the collar in a manner well known to those skilled in the art, such as by means of a suitable medical grade adhesive.

Figure 3:
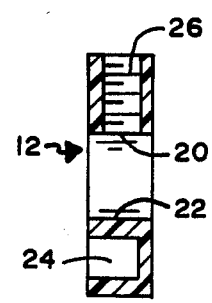
FIG. 3 is a sectional view of the collar in FIG. 2, taken along the lines III—III.

The collar includes a slot 16 for receipt of a surgical pin P, such as a halo pin, external fixation pin, traction pin, or surgical wire. Thus, when the term "surgical pin" is used herein, it includes surgical wires, as well as surgical pins, and such devices as those mentioned above. Slot 16 comprises a bottom side 18, a top side 20, and a corner 22 adjacent to the bottom side. Preferably, the collar also includes a tooling recess 24, shown in FIGS. 2 and 3, to reduce the weight of the collar as well as to reduce the material required to fabricate the collar, leading to reduced manufacturing costs. Tooling recess 24 preferably includes ribs 25 for increasing the structural rigidity of collar 12.

The pin site shield further includes means for securing surgical pin P in slot 16; in the preferred embodiment, the collar further includes a tapped hole 26 passing through the top side 20 of the slot, and the means for securing the surgical pin in the slot comprises a screw 28 inserted into tapped hole 26. As shown in FIG. 8, the screw typically has knurling 30 and 8-32 threads 32. Optionally, the means for securing the surgical pin in the slot further comprises a nib 34 on the bottom side of the slot for assisting in the entrapment of large surgical pins within the slot. In the preferred embodiment, the means for securing the surgical pin in the slot is improved by having angle 36 formed by the tapped hole with respect to the slot be an acute angle, enabling more positive entrapment of the surgical pin in corner 22 of the slot when screw 28 is in a fully inserted position, and allowing a wide range of sizes of surgical pins, from large traction pins to small surgical wires, to be used with a single size pin site shield. Although the means for securing the surgical pin in the slot has been described as including a screw, other means may be used to secure the pin in the slot without departing from the spirit and scope of the present invention.

Figure 5:
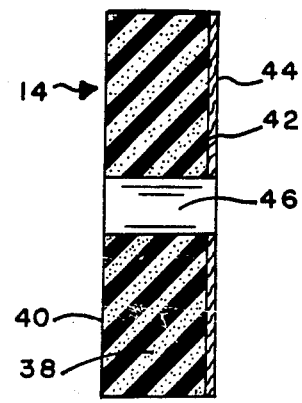
FIG. 5 is a sectional view of the surgical sponge in FIG. 4, taken along the lines V—V.

Surgical sponge 14 comprises a foam pad 38 having a side 40 adjacent to the collar and a side 42 remote from the collar as shown in FIGS. 5 and 6. The surgical sponge further comprises a tricot material 44 attached to the foam pad on the side 42 remote from the collar. FIG. 6 shows a cross section of a portion of the surgical sponge, showing the construction of tricot material attached to the foam pad in a manner well-known to those skilled in the art. Typically, the attachment is accomplished by means of heat bonding, such as by means of a heated layer of mylar plastic placed between the tricot material and the foam pad. The surgical sponge has an opening 46 therethrough, located substantially in the center of the sponge, and a slit 48 extending outwardly from opening 46 and in substantial registration with slot 16 in the collar when the surgical sponge is attached to the collar, allowing the surgical pin to pass inwardly and outwardly within the slot. In the preferred embodiment of the surgical sponge, opening 46 comprises one or more substantially radial cuts 50 as shown in FIG. 7. Tricot material 44 enhances absorption of antiseptic, such as betadine or a saline solution, by the sponge, and is placed next to the skin S of the patient as shown in FIG. 9. Preferably, foam pad 38 is constructed from reticulated polyurethane having 70 to 90 pores per inch, well known to those skilled in the art.

The materials chosen for construction of the pin site shield are preferably selected to be suitable for both gas and radiation sterilization.

The collar and the screw are preferably constructed of plastic or nylon, well known to those skilled in the art.

The use of pin site shields 10 is shown in FIG. 9 in connection with a surgical pin P passing through a bone B within patient's limb L, portions of which have been cut away for purpose of illustration. Slit 48 in the surgical sponge, while allowing a surgical pin, such as surgical pin P, to pass inwardly within slot 16 in collar 12, also allows for ease of installation of pin site shield 10. As pin P becomes fully seated within the interior portion of slot 16, sponge 14, which necessarily became compressed in the region surrounding slit 48 to allow passage of the pin, expands to assume its normal relaxed position, thus assisting in holding the pin in the slot while pin site shield 10 is secured to the pin, allowing rapid installation of the device using only one hand. In the preferred embodiment of the surgical sponge, the material surrounding the multiplicity of cuts 50 similarly assists in holding pin P in slot 16 during installation of the pin site shield.

When pin site shield 10 has been secured to surgical pin P, with surgical sponge 14 pressing against the skin S of the patient as shown in FIG. 9, the soft tissue T around the entry or exit site of the wound W is stabilized and prevented from excessive movement as the patient changes position due to the positive means securing the pin site shield 10 to the surgical pin P, thus reducing the incidence of infection and promoting healing. Antiseptic, such as betadine or a saline solution, which has been applied to the surgical sponge 14, is supplied to the pin site wound due to the substantially close contact maintained between the surgical sponge and the patient's skin. The pin site shield 10 also conceals the unsightly appearance of the surgical pin site wound W, thus reducing psychological trauma in some patients, especially children. The reduction in time required to change the pin site shield compared to the prior art, together with the concealment of the pin site wound W, tends to increase the patient compliance with a required daily changing of the dressing.

Although the present invention has been described and illustrated with respect to a preferred embodiment and a preferred use therefor, it is not to be so limited since modifications and changes can be made therein which are within the full intended scope of the invention.

I claim:

1. A pin site shield for attachment to a surgical pin, comprising:
   (a) a collar having a slot for receipt of the surgical pin;
   (b) a surgical sponge attached to said collar, said surgical sponge comprising
     a foam pad having a side adjacent to said collar and a side remote from said collar, and
     a tricot material attached to said foam pad on said side remote from said collar,
     said surgical sponge having a slit in substantial registration with said slot in said collar, allowing the surgical pin to pass inwardly and outwardly within said slot; and,
   (c) means for securing the pin in said slot.

2. A pin site shield as described in claim 1, wherein said slot further includes a top side and a bottom side, and said collar further includes a tapped hole passing through said top side of said slot, and wherein said means for securing the pin in said slot comprises a screw inserted into said tapped hole.

3. A pin site shield as described in claim 2, wherein said slot further comprises a corner adjacent to said bottom side, and wherein said tapped hole forms an acute angle with respect to said slot for entrapment of the pin in said corner of said slot.

4. A pin site shield as described in claim 2 or claim 3, wherein said means for securing the pin in said slot further comprises a nib on said bottom side of said slot.

5. A pin site shield as described in claim 1, wherein said foam pad is constructed from reticulated polyurethane.

6. A pin site shield as described in claim 5, wherein said tricot material has been attached by means of heat bonding to said foam pad.

7. A pin site shield as described in claim 6, wherein said slot further includes a top side and a bottom side, and said collar further includes a tapped hole passing through said top side of said slot, and wherein said means for securing the pin in said slot comprises a screw inserted into said tapped hole.

8. A pin site shield as described in claim 7, wherein said means for securing the pin in said slot further comprises a nib on said bottom side of said slot.

9. A pin site shield as described in claim 7 or claim 8, wherein said slot further comprises a corner adjacent to said bottom side, and wherein said tapped hole forms an acute angle with respect to said slot for entrapment of the pin in said corner of said slot.

* * * * *